United States Patent
Schilke et al.

(10) Patent No.: US 7,160,932 B2
(45) Date of Patent: Jan. 9, 2007

(54) BONE CEMENT HAVING IMPROVED MECHANICAL PROPERTIES, AND PROCESS FOR THE PREPARATION THEREOF

(75) Inventors: Frank Schilke, Weiterstadt (DE); Berthold Nies, Fraenkisch-Crumbach (DE); Brigitte Jeschke, Kelkheim (DE); Matthias Koch, Wiesbaden (DE); Armin Kuebelbeck, Bensheim (DE)

(73) Assignee: Biomet Deutschland GmbH, Berlin (DE)

( * ) Notice: Subject to any disclaimer, the term of this patent is extended or adjusted under 35 U.S.C. 154(b) by 587 days.

(21) Appl. No.: 10/737,793

(22) Filed: Dec. 18, 2003

(65) Prior Publication Data

US 2004/0127597 A1    Jul. 1, 2004

(30) Foreign Application Priority Data

Dec. 20, 2002  (DE) .................... 102 60 918

(51) Int. Cl.
| | |
|---|---|
| *A61F 2/28* | (2006.01) |
| *A61K 6/083* | (2006.01) |
| *C08K 9/00* | (2006.01) |
| *C08K 3/22* | (2006.01) |
| *C08K 3/36* | (2006.01) |
| *C08F 20/10* | (2006.01) |

(52) U.S. Cl. ............... 523/117; 523/200; 526/318; 524/408; 524/423; 524/431

(58) Field of Classification Search ............... 523/117, 523/200; 524/431
See application file for complete search history.

(56) References Cited

U.S. PATENT DOCUMENTS

| | | | |
|---|---|---|---|
| 5,650,108 A * | 7/1997 | Nies et al. ............. | 264/122 |
| 5,795,922 A | 8/1998 | Demian et al. | |
| 5,902,839 A * | 5/1999 | Lautenschlager et al. ... | 523/115 |
| 6,080,801 A | 6/2000 | Draenert et al. | |
| 2004/0157952 A1* | 8/2004 | Soffiati et al. ............. | 523/115 |

FOREIGN PATENT DOCUMENTS

| | | |
|---|---|---|
| DE | 4029714 | 3/1992 |
| EP | 0041614 | 5/1981 |

* cited by examiner

*Primary Examiner*—Tae H Yoon
(74) *Attorney, Agent, or Firm*—Millen, White, Zelano, Branigan, P.C.

(57) ABSTRACT

Bone cements containing polyacrylates or polymethacrylates and an X-ray contrast medium can be prepared by functionalizing the X-ray contrast medium with (meth) acrylate groups prior to being coating with melamine-formaldehyde resin and subsequent polymerization. The invention resultant bone cement can be used for anchoring prosthesis components in bone, for stiffening bone, as bone screw fixing plug and as implants for anchoring screws.

26 Claims, No Drawings

BONE CEMENT HAVING IMPROVED MECHANICAL PROPERTIES, AND PROCESS FOR THE PREPARATION THEREOF

The invention relates to a process for the preparation of bone cements from polyacrylates or polymethacrylates using an X-ray contrast medium, in which the X-ray contrast medium is functionalised with (meth)acrylate groups with prior coating with melamine resin. The invention furthermore relates to a bone cement containing polyacrylates or polymethacrylates, and an X-ray contrast medium, and to the use thereof for anchoring prosthesis components in bone, for stiffening bone, as bone screw fixing plug or as implant for anchoring screws.

Implants are fixed in bone using bone cements. These consist substantially of polyacrylates or polymethacrylates, preferably polymethyl methacrylate (PMMA). In order to render the materials visible in X-ray images, X-ray contrast media are admixed; these are frequently zirconium oxide. The $ZrO_2$ does not form a chemical bond with the poly (meth)acrylate matrix. The particles of contrast media, which usually have a diameter of from 10 to 50 μm, are loosely enclosed by the polymer. This can result in reduced fracture resistance of the material.

The prior art discloses the admixing of X-ray contrast materials (generally $ZrO_2$ or $BaSO_4$) with a powder consisting of PMMA or PMMA copolymer beads and a polymerisation initiator. The resultant powder component is, for polymerisation, mixed with a monomer liquid (generally methyl methacrylate) in which an activator component is present. Since the said X-ray contrast media tend to be hydrophilic, they are neither physically nor chemically bonded to the hydrophobic polymer matrix during the polymerisation. These particles are therefore loosely enclosed by the polymer, giving rise to a weakening of the material strength.

Since the X-ray contrast medium is not bonded to the polymer matrix, it can be released to the surrounding biological tissue. Owing to the toxicity, in particular of barium sulfate, this contamination is undesired. Thus, Sabokbar and Fujikawa (The Journal of Bone and Joint Surgery, Vol. 79-B, No. 1 (1997)) describe that liberated X-ray contrast medium ($ZrO_2$ and in particular $BaSO_4$) can result in osteolysis. This effect has not been observed in PMMA cement without X-ray contrast medium.

In addition, the liberation of hard zirconium particles at the interface between cement and metal implant is regarded as a cause of prosthesis loosening due to mechanical abrasion.

DE 4029714 (Draenert) describes a process in which X-ray contrast media (filler particles) are incorporated into a melt of the PMMA polymer, and polymer beads are subsequently produced by precipitation of this melt in a precipitation bath, with at least some of these beads embedding the X-ray contrast medium. Owing to their different surface structure, however, precipitated polymer beads also have different mechanical and swelling properties from the bead polymers usually used in bone cement. It is disadvantageous that some of the X-ray contrast medium is located at the surface of the PMMA beads in this process, meaning that mechanical abrasion is not eliminated thereby.

EP 089782 (U.S. Surgical Corp.) describes a process for the production of a porous implantable prosthesis in which an X-ray contrast medium (barium sulfate) is incorporated into polymer particles. In contrast to the process according to the invention, the X-ray contrast medium is not polymerised into PMMA, but instead is bonded to existing PMMA particles by means of 4–7% of hydroxyethyl methacrylate. This $BaSO_4$/poly(hydroxyethyl methacrylate) coating does not meet the requirements made of a bone cement. It is therefore merely employed as pulverulent X-ray-opaque filler material for bone defects.

U.S. Pat. No. 5,795,922 (Demian et al.) discloses a process for the production of polymer beads with embedded X-ray contrast media. The precipitation described here of PMMA onto barium sulfate particles from a solvent and subsequent polymerisation into PMMA beads differs fundamentally from the process according to the invention.

EP 581 387 (BMS) describes a process in which polymer particles produced by precipitation or melting of a polymer onto X-ray contrast medium particles are embedded in polymer beads in a further step.

EP 041614 (Bayer AG) discloses a process in which the X-ray contrast medium barium sulfate is coated by precipitation of a (meth)acrylic acid copolymer dissolved in a solvent. However, this material is unsuitable for use in bone cements owing to its chemical composition.

U.S. Pat. No. 4,500,658 (Austenal Int., Inc.) describes a process for the production of radio-opaque acrylic particles in bead form, in which the compatibilisation of the X-ray contrast medium is carried out in situ during the bead polymerisation by means of suitable silanisation agents.

An object of the present invention is to provide a process and a bone cement which avoid the above-mentioned disadvantages of the prior art.

Upon further study of the specification and appended claims, further objects and advantages of this invention will become apparent to those skilled in the art.

These objects are achieved by the process and the bone cement according to the invention.

The functionalisation according to the invention of inorganic filler materials, such as $ZrO_2$ and $BaSO_4$, with (meth) acrylate groups allows chemical bonding to the surrounding polymer of the hardened bone cement. The added material is thus not loosely incorporated into the matrix for an extended period, but instead is a permanent constituent thereof. This results in it no longer being possible for microcracks to propagate along the boundary between the inorganic particles and the matrix. Furthermore, this modification increases the abrasion resistance of the cement, which reduces liberation of the filler materials into the surrounding tissue and prevents long-term contamination of the PE wear surfaces of implants with X-ray contrast media. It has, surprisingly, now been found that the ability of the X-ray contrast medium to be incorporated into the cement is also improved by the modification. In order to be able to attach acrylate groups to the X-ray contrast medium, prior coating with melamine resin as reactive interlayer is necessary. Melamine resin-coated particles have, surprisingly, significantly greater reactivity than uncoated material.

The process according to the invention for the preparation of bone cements from polyacrylates or polymethacrylates using an X-ray contrast medium is characterised by functionalisation of this contrast medium with (meth)-acrylate groups in accordance with the following steps:

a) suspension of the solid X-ray contrast medium in water and subsequent heating,
b) addition of melamine-formaldehyde resin and an acid, preferably formic acid,
c) washing and drying of the melamine-coated particles,
d) addition of (meth)acryloyl chloride with stirring,
e) washing and drying of the X-ray contrast medium that has been functionalised with reactive (meth)acrylate groups.

In step a) the suspension is preferably heated to 30–95° C., especially 70–90° C. Also, in step a) any suitable suspension medium can be used that will permit the coating of the contrast particles with the melamine-formaldehyde resin to proceed can be used. Aqueous mediums, e.g., water, are preferred.

In step b) the melamine-formaldehyde resin is, for example, the condensation product of cyanurictriamde and formaldehyde with a cyanurictriamde: formaldehyde molar ratio of 1:1–6. Also, in step b0 the weight ratio of resin to contrast medium is preferably 0.01:100 to 100:1, especially 0.1:1 to 1:1. For step b) essentially any acid can be used, although formic acid, acetic acid and p-toluene sulphuric acid are preferred. In steps c) and e) washing is preferably performed using water (for example, in a buchner funnel) and the particles are preferably dried in air, more preferably dried under vacuum with heating, for example, at 50° C.

In step d) (meth)acryloyl chloride is preferably used. However, in general any acrylic acid derivative that is able to react with OH-groups is suitable (for example, halides, anhydrides, azides and esters) including acrylic acid and substituted acrylic acids themselves. Specific examples include (meth)acryloyl chloride, acrylic acid, methacrylic acid, acrylic anhydride, and methacrylic anhydride.

As bone cement, use is made of polyacrylates or polymethacrylates, in particular PMMA. Preferably, the number molecular weight of the polyacrylate or polymethacrylate is 1,000–100,000 g/mol, especially 5,000–30,000 g/mol.

In the X-ray contrast medium, which has the job of absorbing X-rays and thereby rendering material visible in corresponding photographs, only the amount (mass) of material employed plays a role. It is preferably between 8 and 16% by weight of the mass of the cement powder.

X-ray contrast media which can be used are conventional particles having a diameter in the range from 0.5 to 50 μm. However, preference is given to nanoscale material having a particle size of from 5 to 500 nm, which is selected in order further to improve the material properties. This results in a significantly more uniform distribution of the inorganic particles in the polymer matrix. For the same added amount, the flaws are smaller by a factor of 500–1000, significantly reducing their adverse effect on the strength of the material.

Preference is given to the use of $ZrO_2$, $BaSO_4$ or bismuth-containing or iodine-containing contrast media. Particular preference is given to $ZrO_2$.

The bone cements according to the invention can be used for anchoring prosthesis components in bone and for stiffening bone. They can further-more also be used as bone screw fixing plugs or as implants for anchoring screws.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. 10260918.7, filed Dec. 20, 2002 is hereby incorporated by reference.

EXAMPLE

Functionalisation of zirconium oxide with acrylate groups:

250 g of zirconium oxide (MERCK 100757) are suspended in 4 l of water and warmed to 70° C. 80 g of Madurit® SMW818 (=melamine-formaldehyde resin) and 150 ml of formic acid (w=2%) are added. The mixture is stirred at 70° C. for a further 30 minutes before being allowed to cool to room temperature. The melamine-coated particles are washed and dried. 200 g of this powder are stirred overnight at room temperature in 150 ml of acryloyl chloride, separated from the remaining acrylic acid, washed with sodium hydroxide solution and water until neutral and dried under reduced pressure at room temperature, giving a free-flowing powder of zirconium oxide with reactive acrylate groups on the surface which can be free-radical-copolymerised with acrylates.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the preparation of a bone cement comprising polymerizing an acrylate or methacrylate to form a polyacrylate or polymethacrylate, wherein prior to polymerization, said acrylate or methacrylate is combined with an X-ray contrast medium which is functionalized with (meth)acrylate groups by prior coating with melamine-formaldehyde resin.

2. A process according to claim 1, wherein functionalization of said X-ray contrast medium with (meth)acrylate groups comprises:
   a) suspending solid X-ray contrast medium in water and subsequently heating the resultant suspension,
   b) adding melamine-formaldehyde resin and an acid to said suspension,
   c) washing and drying the resultant melamine- formaldehyde resin-coated X-ray contrast medium particles,
   d) adding (meth)acryloyl chloride with stirring,
   e) washing and drying of the X-ray contrast medium that has been functionalized with reactive (meth)acrylate groups.

3. A process according to claim 1, wherein said X-ray contrast medium used is a nanoscale contrast medium having a particle size of 0.5 to 50 μm.

4. A process according to claim 2, wherein said X-ray contrast medium used is a nanoscale contrast medium having a particle size of 0.5 to 50 μm.

5. A process according to claim 1, wherein said X-ray contrast medium has a particle size of 5 to 500 nm.

6. A process according to claim 2, wherein said X-ray contrast medium has a particle size of 5 to 500 nm.

7. A process according to claim 1, wherein said X-ray contrast medium is employed in an amount of 8–16% by weight, based on the overall mass of the bone cement.

8. A process according to claim 2, wherein said X-ray contrast medium is employed in an amount of 8–16% by weight, based on the overall mass of the bone cement.

9. A process according to claim 3, wherein said X-ray contrast medium is employed in an amount of 8–16% by weight, based on the overall mass of the bone cement.

10. A process according to claim 4, wherein said X-ray contrast medium is employed in an amount of 8–16% by weight, based on the overall mass of the bone cement.

11. A process according to claim 5, wherein said X-ray contrast medium is employed in an amount of 8–16% by weight, based on the overall mass of the bone cement.

12. A process according to claim 6, wherein said X-ray contrast medium is employed in an amount of 8–16% by weight, based on the overall mass of the bone cement.

13. A process according to claim 1, wherein said X-ray contrast medium $ZrO_2$, $BaSO_4$ or bismuth-containing or iodine-containing contrast media.

14. A process according to claim 1, wherein said X-ray contrast medium $ZrO_2$.

15. A bone cement comprising polyacrylates or polymethacrylates and an X-ray contrast medium, wherein said X-ray contrast medium has a particle size of 5 to 500 nm and the particles of said contrast medium are functionalised with (meth)acrylate groups by coating with melamine-formaldehyde resin prior polymerization to form said polyacrylates or polymethacrylates.

16. A bone cement according to claim 15, wherein the amount of X-ray contrast medium is 8–16% by weight, based on the overall mass of the bone cement.

17. A bone cement according to claim 15, wherein said X-ray contrast medium is zirconium dioxide ($ZrO_2$), barium sulfate ($BaSO_4$) or a bismuth-containing or iodine-containing contrast medium.

18. A bone cement according to claim 16, wherein said X-ray contrast medium is zirconium dioxide ($ZrO_2$), barium sulfate ($BaSO_4$) or a bismuth-containing or iodine-containing contrast medium.

19. A bone cement according to claim 15, wherein said X-ray contrast medium $ZrO_2$.

20. In a process for anchoring prosthesis components in bone using a bone cement or for stiffening bone using a bone cement, the improvement wherein said bone cement is a bone cement according to claim 15.

21. In a bone screw fixing plug comprising a bone cement or an implant for anchoring screws comprising a bone cement, the improvement wherein said bone cement is a bone cement according to claim 15.

22. A process according to claim 1, wherein functionalization of said X-ray contrast medium with (meth)acrylate groups comprises:

a) suspending solid X-ray contrast medium in a suspension medium and subsequently heating the resultant suspension, b) adding melamine-formaldehyde resin and an acid to said suspension, c) washing and drying the resultant melamine-formaldehyde resin-coated X-ray contrast medium particles, d) adding (meth)acrylic acid or a (meth)acrylic acid halide, anhydride, azide or ester with stirring, e) washing and drying of the X-ray contrast medium that has been functionalized with reactive (meth)acrylate groups.

23. A process according to claim 22, wherein in step a) said suspension is heated to 30–95° C.

24. A process according to claim 22, wherein in step b) the weight ratio of resin to contrast medium is 0.1:1–1:1.

25. A process according to claim 22, wherein in step b) said acid is formic acid, acetic acid, p-toluene sulphuric acid.

26. A process according to claim 22, wherein in step b) wherein said resin has a number molecular weight of 5,000–30,000 g/mol.

* * * * *